United States Patent [19]

Howard et al.

[11] Patent Number: 4,639,669

[45] Date of Patent: Jan. 27, 1987

[54] PULSED ELECTROMAGNETIC NONDESTRUCTIVE TEST METHOD FOR DETERMINING VOLUME DENSITY OF GRAPHITE FIBERS IN A GRAPHITE-EPOXY COMPOSITE MATERIAL

[75] Inventors: Darryl A. Howard, Sunnyvale; Lawrence Y. L. Shen, Saratoga, both of Calif.

[73] Assignee: Lockheed Missiles & Space Company, Inc., Sunnyvale, Calif.

[21] Appl. No.: 535,576

[22] Filed: Sep. 26, 1983

[51] Int. Cl.$^4$ .......................... G01N 9/24; G01R 33/12
[52] U.S. Cl. ..................................... 324/239; 324/229; 324/58.5 A; 73/32 R; 73/597
[58] Field of Search .............................. 324/228-243, 324/260-262, 58 A, 58.5 A, 207, 208, 338; 73/32 R, 32 A, 597

[56] References Cited

U.S. PATENT DOCUMENTS

| | | |
|---|---|---|
| 2,939,073 | 5/1960 | Eul, Jr. |
| 3,189,817 | 6/1965 | Renken, Jr. .................... 324/240 |
| 3,205,485 | 9/1965 | Noltingk ........................ 324/207 |
| 3,350,634 | 10/1967 | Hoehn, Jr. ..................... 324/338 |
| 3,718,855 | 2/1973 | Rogel et al. |
| 3,810,005 | 5/1974 | Bennion et al. ............... 324/58.5 A |
| 3,890,564 | 6/1975 | Watanabe et al. ............. 324/233 X |
| 3,984,895 | 10/1976 | Grice, Jr. ....................... 73/32 A X |
| 4,006,405 | 2/1977 | Greenwood et al. ......... 324/229 X |
| 4,107,606 | 8/1978 | Typpo et al. .................. 324/229 |
| 4,123,702 | 10/1978 | Kinanen et al. ............... 324/58.5 A |
| 4,217,774 | 8/1980 | Agar .............................. 73/32 A |
| 4,220,915 | 9/1980 | Kawamoto et al. ........... 324/58 A |
| 4,230,987 | 10/1980 | Mordwinkin ................. 324/236 |
| 4,235,099 | 11/1980 | Ishizaka ......................... 73/32 A |
| 4,351,031 | 9/1982 | Flaherty et al. ............... 364/580 |
| 4,446,735 | 5/1984 | Weilacher ...................... 73/597 |
| 4,481,820 | 11/1984 | Thomann ....................... 73/597 |
| 4,570,486 | 2/1986 | Volkmann ..................... 73/597 |

OTHER PUBLICATIONS

Dodd, "Applications of a Phase-Sensitive Eddy Current Instrument", Materials Evaluation, Jun. 1969, pp. 260-262/272.
Dodd, "A Portable Phase-Sensitive Eddy Current Instrument", Materials Evaluation, Mar. 1968, pp. 33-36.
Dodd et al., "Thickness Measurements Using Eddy Current Techniques", Materials Evaluation, May 1973, pp. 73-79/84.

Primary Examiner—Reinhard J. Eisenzopf
Assistant Examiner—Warren S. Edmonds
Attorney, Agent, or Firm—John J. Morrissey

[57] ABSTRACT

A procedure for nondestructively determining a physical characteristic of a test object (10) involves introducing an electromagnetic energy pulse into the test object, and measuring elapsed time before the signature of a time-dependent function of the energy thereby propagated through the test object (10) reaches a value larger than a pre-set threshold value. For example, the volume density of graphite fibers in a graphite-epoxy composite material can be determined by introducing a pulse of radio-frequency electromagnetic energy into the composite material, and by measuring the elapsed time before the voltage signature of the energy propagated through the composite material reaches a value larger than the threshold value.

3 Claims, 1 Drawing Figure

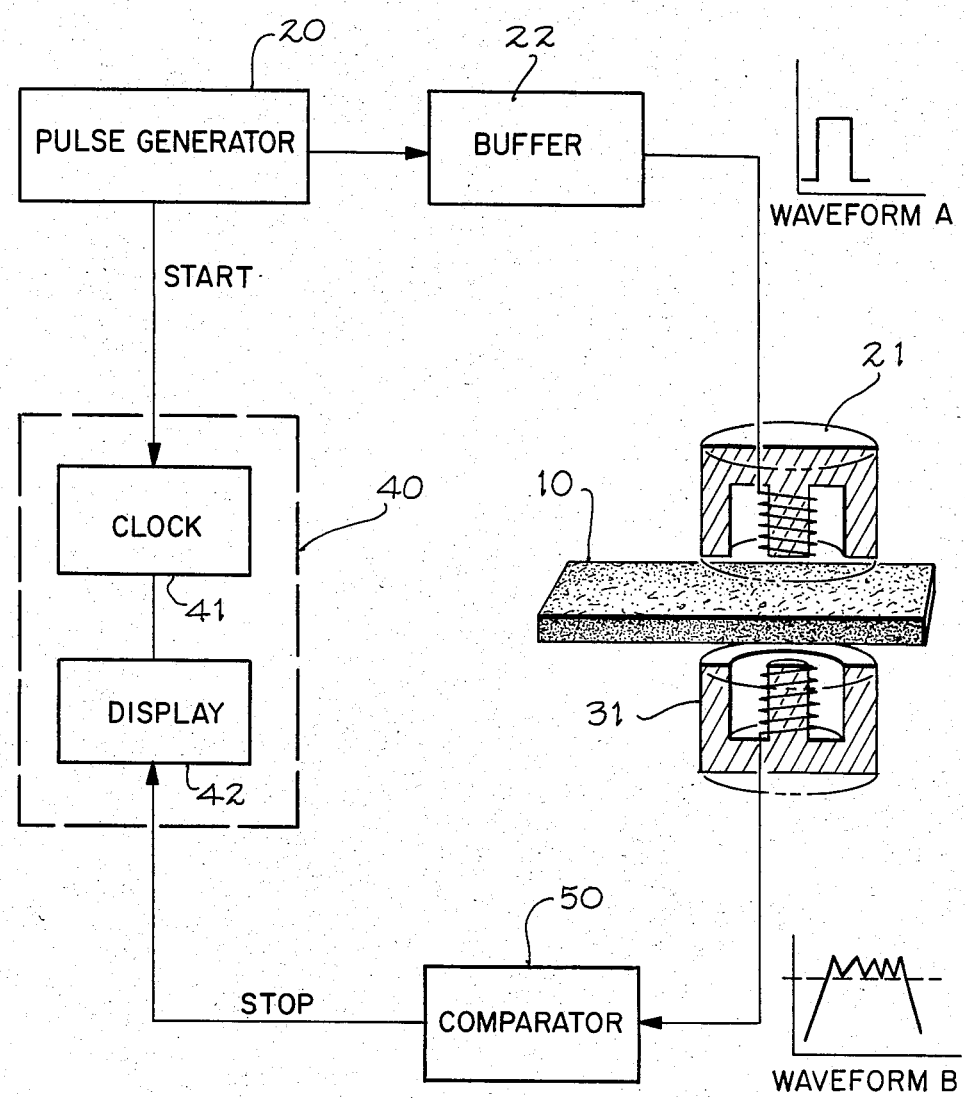

PULSED ELECTROMAGNETIC NONDESTRUCTIVE TEST METHOD FOR DETERMINING VOLUME DENSITY OF GRAPHITE FIBERS IN A GRAPHITE-EPOXY COMPOSITE MATERIAL

TECHNICAL FIELD

This invention relates generally to nondestructive testing, and more particularly to nondestructive testing techniques involving signature analysis of pulses of electromagnetic energy transmitted through test objects.

BACKGROUND ART

Eddy current techniques have been used for many years to inspect electrically conductive materials. Useful background information regarding the technology of nondestructive testing by eddy current techniques can be found in published articles such as: "Applications of a Phase Sensitive Eddy Current Instrument" by C. V. Dodd in *Materials Evaluation*, June 1964, pp. 260–262/272; "A Portable Phase-Sensitive Eddy Current Instrument" by C. V. Dodd in *Materials Evaluation*, March 1968, pp. 33–36; and "Thickness Measurements Using Eddy Current Techniques" by C. V. Dodd and W. A. Simpson Jr. in *Materials Evaluation*, May 1973, pp. 73–79/84.

Various eddy current techniques for inspecting electrically conductive materials have been described over the years in the patent literature. Representative patents, which indicate pertinent fields of search for investigating the prior art, include U.S. Pat. Nos. 2,939,073; 3,718,855; 4,006,405; 4,107,606; 4,230,987; and 4,351,031.

SUMMARY OF THE PRESENT INVENTION

It is an object of the present invention to provide a technique for inspecting a test object, which may be either metallic or dielectric, by introducing a pulse of radio-frequency electromagnetic energy into the test object and by analyzing the signature of a time-dependent electrical parameter which is a function of the energy thereby propagated through the test object.

It is a specific object of the present invention to provide a technique for nondestructively testing an object by introducing a pulse of radio-frequency electromagnetic energy into the object and by analyzing a time-varying voltage signature, which is a function of the electromagnetic energy thereby propagated through the object.

More specifically, in a nondestructive testing procedure according to the present invention wherein a pulse of radio-frequency electromagnetic energy is introduced into the object to be tested, the voltage signature of the electromagnetic energy thereby propagated through the object is analyzed by measuring the elapsed time before the voltage signature reaches a value in a specified voltage range.

It is a particular object of the present invention to provide an instrument and procedure for nondestructively determining weight percentages of the constituents of a composite material by introducing a pulse of radio-frequency electromagnetic energy into the composite material, and by measuring the elapsed time before the voltage signature of the electromagnetic energy thereby propagated through the composite material reaches a value greater than a pre-set threshold value.

The present invention is particularly suitable as a nondestructive test procedure for measuring weight percentage and/or fiber volume density for graphite fibers in a graphite-epoxy composite. The present invention can also be used to detecting cracks in metallic or non-metallic structures.

DESCRIPTION OF THE DRAWING

The drawing is a block diagram of a nondestructive test instrument according to the present invention.

BEST MODE OF CARRYING OUT THE INVENTION

As illustrated in the drawing, a test object 10 (e.g., a layer of composite material made of graphite and an epoxy resin) is to be examined for conformity to a particular specification (e.g., a specified volume density of graphite fibers in the composite material).

In accordance with the invention, a conventional radio-frequency pulse generator 20 drives a sending transducer 21, which is positioned so as to introduce a pulse of radio-frequency energy into the test object 10. A buffer 22 is provided in series between the pulse generator 20 and the sending transducer 21 to match the impedance of the pulse generator 20 to the impedance of the sending transducer 21. The sending transducer 21 is configured so as to be relatively insensitive to abrupt changes in curvature on the surface of the test object 10, and also to minimize edge effects in the propagation of the energy pulse through the test object 10.

A receiving transducer 31 is positioned on the opposite side of the test object 10 from the sending transducer 21. In general, the receiving transducer 31 has the same configuration as the sending transducer 21. In the preferred embodiment of the invention for use in measuring the volume density of graphite fibers in a graphite-epoxy composite material, each of the transducers 21 and 31 comprises a low-capacitance coil winding around a cup-shaped ferrite core. When the sending transducer 21 is energized, the coil windings produce a localized electromagnetic field extending through the test object 10. The transducers 21 and 31 are preferably mounted on steel yokes for electromagnetic shielding and mechanical stability.

As illustrated by waveform A in the drawing, the radio-frequency energy pulse introduced by the sending transducer 21 into the test object 10 is a signal having a substantially square waveform. The leading edge of this pulse is used to trigger the "START" channel of a high-frequency counter 40, which is activated by the pulse generator 20. The counter 40 comprises a clock 41 for measuring elapsed time, and a display device 42 for displaying the elapsed time measurement.

If the test object 10 is an electrical conductor, the H-field component of the radio-frequency energy absorbed by the conductor generates eddy currents in the conductor. The eddy currents propagate electromagnetic energy through the test object 10 to the receiving transducer 31. If the test object 10 is a dielectric, the E-field component of the radio-frequency energy absorbed by the dielectric causes the molecules of the dielectric to become polarized. The polarized molecules propagate electromagnetic energy through the test object 10 to the receiving transducer 31. In either case, regardless of whether the test object 10 is a conductor or a dielectric, electromagnetic energy is propagated through the test object 10 to the receiving transducer 31. Certain materials, such as graphite-epoxy composite materials, comprise both conducting and dielectric constituents.

The electromagnetic energy propagated through the test object 10, whether attributable to eddy currents or to polarization, or to both modes of propagation, is detected by the receiving transducer 31 as a signal having a waveform (as indicated by waveform B in the drawing) that is the sum of the contributions due to the operable modes of energy propagation for the particular material of which the test object 10 is made.

The signal received by the receiving transducer 31 is amplified by a comparator 50. The output of the comparator 50 is used to trigger the "STOP" channel of the counter 40. The elapsed time (also called "delay time") required for transmission of the energy through the test object 10, as measured by the clock 41, is displayed by the display device 42.

The shape of waveform B (i.e., the voltage signature of the energy transmitted through the test object 10) is a characteristic of the test object 10. Thus, if the voltage signature of the energy transmitted through the test object 10 by a pulse of a given waveform differs from the voltage signature of the energy transmitted through a reference object by an identical pulse, it may be concluded that the test object 10 differs from the reference object in some physical characteristic. This feature of the voltage signature, or of the signal of any other time-dependent electrical parameter that is a function of the energy propagated through test object 10, provides the basis for a quality-control procedure whereby test objects that differ from a reference object can be identified.

Comparison of elapsed time required for propagation of a radio-frequency energy pulse through a reference object with elapsed time required for propagation of an identical pulse through a test object is a convenient way to analyze the voltage signature of the energy propagated through the test object, and is the preferred procedure for practicing the present invention.

In one particular application of the present invention, the volume density of graphite fibers in a graphite-epoxy composite material can be measured directly in terms of the time required for a pulse of radio-frequency electromagnetic energy to be propagated through the composite material. It has been found by experimentation that the time required for a pulse of radio-frequency energy to be propagated through a panel of graphite-epoxy composite material is substantially linearly proportional to the volume density of graphite fibers in the composite material. Measurements made by the "elapsed time" technique for determining the volume density of graphite fibers in a graphite-epoxy composite material substantially agree with volume density measurements made by conventional chemical analysis.

An apparatus in accordance with the present invention can also be used as a quality-control instrument for detecting cracks or inhomogeneities in metallic or nonmetallic structures. In operation, as the structure to be tested is scanned by the transducers 21 and 31, the occurrence of a crack or inhomogeneity in the structure is indicated by the display device 42 as a localized delay-time anomaly. In a further application, the spatial distribution of delay times obtained by scanning different regions of the test structure with the transducers 21 and 31 can be plotted to form an image of the test structure.

A particular embodiment of a nondestructive test instrument in accordance with the present invention has been described herein. However, other embodiments suitable for particular applications would become apparent to workers skilled in the art upon perusal of the foregoing specification and accompanying drawing. The description of the instrument and test procedure presented herein is illustrative of the invention, which is more generally defined by the following claims and their equivalents.

We claim:

1. A method for nondestructively determining volume density of graphite fibers in a sample of graphite-epoxy composite material, said sample conforming in volume to a reference piece of graphite-epoxy composite material for which the volume density of graphite fibers is known, said method comprising the steps of:
    (a) inductively coupling a first pulse of radio-frequency electromagnetic energy into said reference piece;
    (b) receiving energy propagated through said reference piece due to said first pulse;
    (c) measuring elapsed time before a time-dependent function of said energy propagated through said reference piece due to said first pulse reaches a value larger than a pre-set threshold value;
    (d) inductively coupling a second pulse of radio-frequency electromagnetic energy into said sample, said second pulse being substantially identical in waveform to said first pulse;
    (e) receiving energy propagated through said sample due to said second pulse;
    (f) measuring elapsed time before a time-dependent function of said energy propagated through said sample due to said second pulse reaches a value larger than said pre-set threshold value; and
    (g) calculating a ratio of said elapsed time before said time-dependent function of energy propagated through said sample reaches said threshold value to said elapsed time before said time-dependent function of energy propagated through said reference piece reaches said threshold value, said ratio being substantially equal to the ratio of volume density of graphite fibers in said sample to volume density of graphite fibers in said reference piece.

2. The method of claim 1 wherein said time-dependent function of energy is voltage.

3. The method of claim 2 wherein said energy propagated through said reference piece due to said first pulse is received as a first voltage signature and said energy propagated through said sample due to said second pulse is received as a second voltage signature, and wherein the ratio of volume density of graphite fibers in said sample to volume density of graphite fibers in said reference piece is determined from the ratio of the elapsed time required for said second voltage signature to reach said threshold value to the elapsed time required for said first voltage signature to reach said threshold value.

* * * * *